United States Patent [19]

Canick et al.

[11] Patent Number: 5,605,843
[45] Date of Patent: Feb. 25, 1997

[54] KIT FOR PRENATAL SCREENING FOR DOWN'S SYNDROME

[75] Inventors: Jacob A. Canick, Newton, Mass.; Nicholas J. Wald; Howard S. Cuckle, both of London, United Kingdom; James E. Haddow, Sebago Lake, Me.

[73] Assignee: 3 i Research Exploitation Ltd., United Kingdom

[21] Appl. No.: 478,045

[22] Filed: Jun. 7, 1995

Related U.S. Application Data

[62] Division of Ser. No. 908,875, Jul. 7, 1992, Pat. No. 5,506,150, which is a continuation of Ser. No. 457,687, filed as PCT/GB88/00557 Jul. 11, 1988, abandoned.

[30] Foreign Application Priority Data

Jul. 9, 1987 [GB] United Kingdom .................. 8716158
Oct. 23, 1987 [GB] United Kingdom .................. 8724913

[51] Int. Cl.$^6$ .................. G01N 33/53; G01N 33/74; G01N 33/76
[52] U.S. Cl. .................. 436/510; 435/7.93; 435/975; 436/814; 436/817; 436/818
[58] Field of Search .................. 436/510, 65, 71, 436/127, 131, 814, 817, 818; 435/11, 7.93, 975

[56] References Cited

U.S. PATENT DOCUMENTS

| | | | |
|---|---|---|---|
| 4,208,400 | 6/1980 | Edwards | 436/817 |
| 4,454,232 | 6/1984 | Breglio | 436/504 |
| 4,874,693 | 10/1989 | Bogart | 435/7 |
| 5,506,150 | 4/1996 | Canick et al. | 436/510 |

FOREIGN PATENT DOCUMENTS

| | | | |
|---|---|---|---|
| 0158973 | of 1985 | European Pat. Off. . | |
| WO86/04418 | 7/1986 | WIPO | 436/65 |
| 8604418 | 7/1986 | WIPO | G01N 33/484 |

OTHER PUBLICATIONS

*Prenatal Diagnosis*, vol. 7, 623–630 (1987), Bogart et al "Abnormal Maternal Serum Chorionic Gonadotropin Levels . . .".

*The New England Journal of Medicine*, vol. 317, Aug. 6, 1987, No. 6, pp. 342–346, Schoenfeld DiMaio et al, "Screening for Fetal Down's Syndrome . . .".

*British Medical Journal*, 29 Jun. 1985, 290 (6486) 1925–2002.

*American Journal of Obstetrics and Gynecology*, vol. 148, No. 7, Apr. 1, 1984 Merkatz et al, pp. 886–894, "An Association Between Low Maternal Serum . . .".

"Maternal Serum Alpha–Fetoprotein, Age, and Down Syndrome Risk", Palomaki et al 1986, Foundation for Blood Research, vol. 156, No. 2, pp. 460–463.

*The Lancet*, Oct. 14, 1972, Jorgensen et al, "Low Urinary Oestriol Excretion During Pregnancy in Women . . . " pp. 782–784.

*British Journal of Obstetrics and Gynaecology*, Apr. 1988, vol. 95, pp. 330–333, Canick et al, "Low Second Trimester Maternal Serum Unconjugated . . .".

*British Journal of Obstetrics and Gynaecology*, Apr. 1988, vol. 95, pp. 334–341, Wald et al, "Maternal Serum Unconjugated Oestriol . . . ".

Stryer (1981) Biochemistry 2nd Edition W. H. Freeman & Co, San Francisco pp 464–479.

Kubota et al, 1982, Effect of bromocriptine on the endocrine profile during pregnancy, Acta Obstet Cynaecol Jpn 34(10):1675–83.

Voss et al, 1986. No dependence on the age of biochemical parameters in early pregnancy. Zentralbl Cynaekol 108(20):1217–21.

Furuhashi et al (1984) "Retrograde time scale . . . " Gynecol Obstet Invest 18:264–268.

Canick et al (Oct. 1987) Am. J. Hum. Genetics 41 (3 Suppl.) Abstract 790, 10, 7, p. A269.

Snider (Aug. 1992) USA Today, p. 1.

*Primary Examiner*—Lora M. Green
*Assistant Examiner*—James L. Grun
*Attorney, Agent, or Firm*—Nixon & Vanderhye

[57] ABSTRACT

Kits are provided for prenatal screening tests for risk of Down's syndrome which are carried out on a maternal serum sample obtained before the beginning of the third trimester of pregnancy. The kits contain immunoassay means to determine alpha-fetoprotein, unconjugated oestriol, human chorionic gonadotrophin, and/or dehydroepiandrosterone sulfate (DHEAS).

3 Claims, 2 Drawing Sheets

KIT FOR PRENATAL SCREENING FOR DOWN'S SYNDROME

This is a division of application Ser. No. 07/908,875, filed Jul. 7, 1992 now U.S. Pat. No. 5,506,150, which is a continuation of 07/457,687, filed as PCT/GB00557 on Jul. 11, 1988, now abandoned.

BACKGROUND OF THE INVENTION

This invention relates to antenatal screening for risk of Down's Syndrome in a foetus.

Risk of Down's syndrome in a foetus is known to increase with the age of the mother and it is this fact which forms the basis for selection of mothers for further investigation. Further testing involves sampling of the amniotic fluid by amniocentesis, a procedure which is not completely free from risk to the mother or foetus, induction of miscarriage being a recognised hazard.

The amniotic fluid test for Down's syndrome (the recognition of an extra chromosome 21 in foetal cells) is diagnostic.

There is a need for a screening method which will identify pregnancies most at risk so as to justify amniocentesis with its attendant risks.

An object of the present invention is to provide an improved screening procedure.

DESCRIPTION OF THE INVENTION

According to the present invention there is provided a method of screening for Down's syndrome in a foetus, comprising assaying a sample of maternal serum, taken before the beginning of the third trimester of pregnancy, for at least one serum constituent selected from;

unconjugated oestriol;

progesterone;

16-alpha-hydroxy-dehydroepiandrosterone sulphate (16-alpha-hydroxy-DHEAS);

dehydroepiandrosterone sulphate (DHEAS), and precursors or metabolites thereof, the results of said assay being indicative of increased risk of foetal Down's Syndrome.

The method may also include an additional assay for alpha-fetoprotein.

It is preferred that the method include a further assay for human chorionic gonadotrophin (hCG).

In a particularly preferred method three assays are carried out for alpha-fetoprotein (AFP), unconjugated oestriol and human chorionic gonadotrophin.

In another preferred embodiment the method includes additional assays for either or both of 16-alpha-hydroxy-dehydroepiandrosterone sulphate (16-alpha-hydroxy-DHEAS); and, dehydroepiandrosterone sulphate (DHEAS)

In deriving the risk indicator the assay results may be interpreted in combination with maternal age.

The present invention also provides an assay kit comprising means for conducting the assays for metabolites identified above and means for producing from the said assay results an indication of increased risk of foetal Down's syndrome.

This invention is based on the fact that serum AFP, and unconjugated oestriol ($uE_3$) in maternal blood in early pregnancy are significantly lower in affected pregnancies than unaffected pregnancies, and therefore their precursors including 16-alpha-hydroxy DHEAS and DHEAS are also affected, and serum progesterone and human chorionic gonadotrophin are both greater in affected pregnancies than in unaffected pregnancies.

Figure 1:
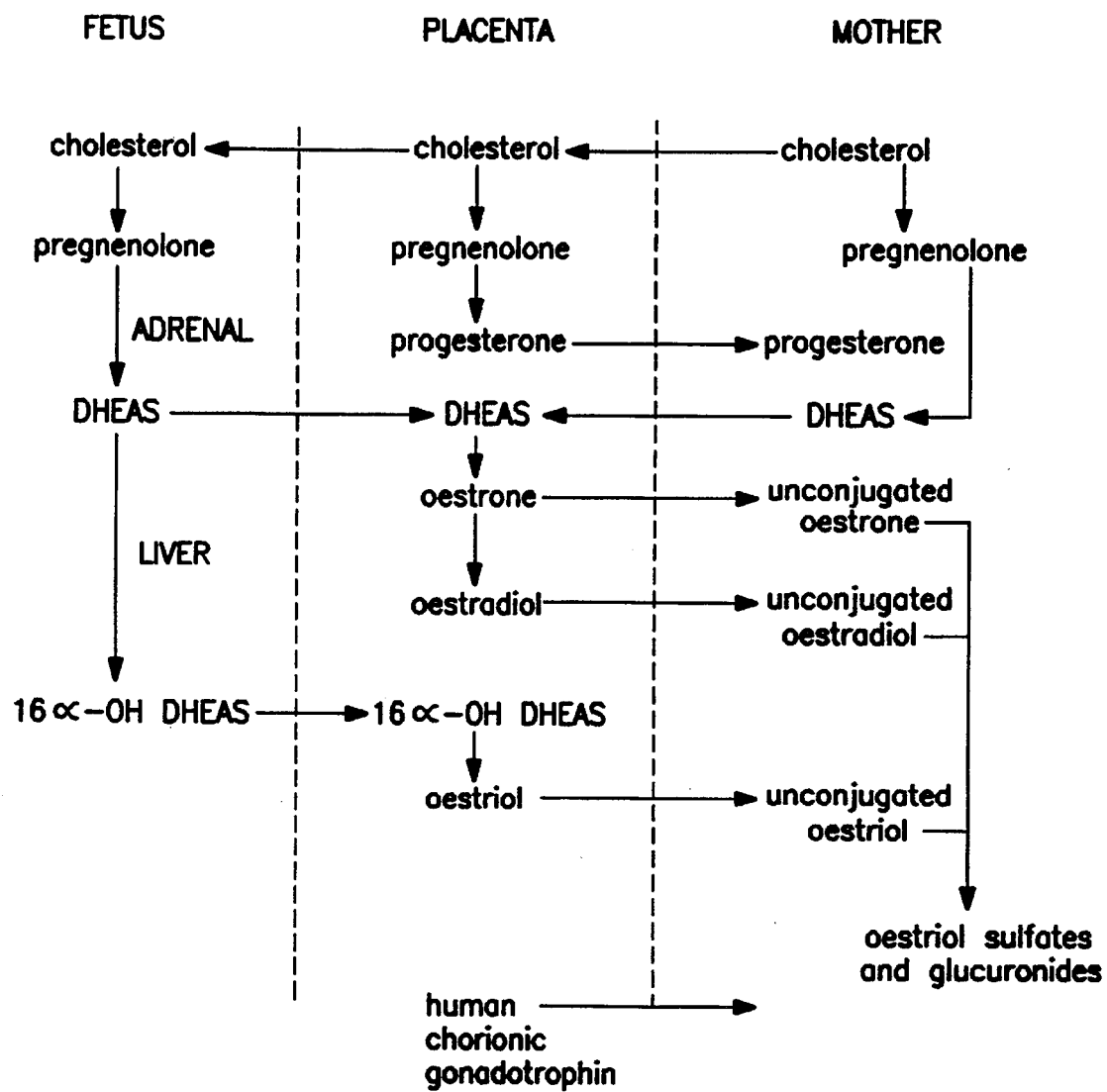
FIG. 1 is a flow chart setting forth the metabolic pathways relating to the biosynthesis of oestriol and progesterone during pregnancy.

The abnormal unconjugated oestriol, progesterone and AFP levels in Down's syndrome pregnancies reflect abnormal synthesis metabolism in the foetus and/or placenta. FIG. 1 of the accompanying drawing sets forth the metabolic pathways relating to the biosynthesis of oestriol (and progesterone) during pregnancy, the oestriol biosynthesis route being shown in bold type. The abbreviations DHEAS means dehydroepiandrosterone sulphate and 16-OH DHEAS means its 16-hydroxy-derivative.

AFP is manufactured by the yolk sac and the foetal liver.

Thus, as shown in FIG. 1, oestriol, derived from cholesterol of maternal origin, is converted, via pregnenolone and DHEAS to 16-hydroxy-DHEAS which is then converted by placental activity to oestriol which returns, in unconjugated form, into maternal serum where, subsequently, it is converted to oestriol sulphates and glucuronides.

Progesterone arises by placenta activity which converts cholesterol to pregnenolone and hence to progesterone, a portion of the pregnenolone being passed to the foetus, for conversion to oestriol by the route described above, and the remainder returned to maternal serum.

The median maternal serum unconjugated oestriol level at 13 to 27 weeks gestation in seventy-seven pregnancies associated with Down's syndrome was 0.73 multiples of the median (MoM) value for 385 unaffected control pregnancies matched for maternal age, gestational age, and duration of storage of the serum sample. This result was statistically highly significant. Serum unconjugated oestriol is a better discriminator between Down's syndrome and unaffected pregnancies than maternal age or serum AFP. The extent of the discrimination was also independent of maternal age and largely independent of serum AFP. When used in combination, the three variables, age, serum AFP and serum unconjugated oestriol, were more effective than any one by itself or two in combination at identifying Down's syndrome. The inclusion of serum progesterone leads to significant increase of the effectiveness of the detection.

The median maternal serum progesterone level at 13 to 27 weeks gestation in 77 pregnancies associated with Down's syndrome was 1.19 multiples of the median value (MoM) for 385 unaffected control pregnancies of the same gestational age. The increase in values was statistically significant ($X_1^2=14$, based on analysis of variance of the ranks of matched sets). There was more overlap in the distribution of progesterone between affected and unaffected pregnancies than was the case for unconjugated oestriol.

In normal pregnancy the foetal adrenal cortex produces DHEAS which enters the foetal circulation and passes to the foetal liver where most of it undergoes 16-alpha-hydroxylation. The newly formed 16-alpha-hydroxy-DHEAS reaches the placenta where a portion of it is converted in four enzymatic steps to oestriol. Unconverted 16-alpha-hydroxy-DHEAS is also likely to pass into the mother's circulation. It is possible that in maternal serum almost all of the 16-alpha-hydroxy-DHEAS is derived from the foetus rather than from the mother, and therefore measurement of this substance is a specific marker of foetal development.

Down's syndrome foetuses are less mature than unaffected foetuses and so pregnancies associated with foetal Down's syndrome would be expected to have lower 16-alpha-hydroxy-DHEAS levels than unaffected pregnancies. It is by similar reasoning that lower levels of DHEAS will be found in the maternal blood of women carrying foetuses with Down's syndrome than in those carrying unaffected foetuses.

Therefore, either or both of DHEAS and 16-alpha-hydroxy-DHEAS provide useful markers of Down's syndrome in early pregnancy, particularly when the results are viewed in combination with the other indicators referred to herein.

The method of the present invention increases the efficiency of screening of women for Down's syndrome by identifying a greater proportion of women with affected pregnancies as eligible for amniocentesis (i.e. increasing the proportion of true positives) without also increasing the proportion of women with unaffected pregnancies who, by some criteria, would be eligible for amniocentesis (i.e. without increasing the proportion of false positives).

The invention will now be described, by way of illustration, in the following description.

DESCRIPTION OF THE PREFERRED EMBODIMENTS

Using a −40° C. antenatal serum bank relating to over 30,000 pregnancies, 77 antenatal serum samples were identified from 77 singleton pregnancies associated with Down's syndrome (cases). Each sample was matched with a stored sample from five unaffected pregnancies (controls) matching for maternal age (within the same year) gestational age (within one week) and duration of storage (within one year) of the sample. The samples were retrieved from storage for unconjugated oestriol and AFP analysis. None of the cases or controls were from pregnancies associated with a neural tube defect, and all the samples were collected between 13 and 27 completed weeks of gestation.

Unconjugated oestriol was assayed using a direct, non-extraction radio-immunoassay (Amerlex oestriol RIA kit, Amersham). The assay was modified by doubling the sample volume to 40 microliters for all the specimens analysed.

Maternal serum AFP was assayed an immuno-radiometric assay (Boots-Celltech Diagnostics Limited).

Maternal serum progesterone was assayed using a radiometric assay (Amerlex-M progesterone (New) kit, Amersham) and serum DHEAS also by radiometric assay (Pantex DHEA-S $I^{125}$ kit).

All the assays were performed within about one week. Cases and controls were always assayed in the same analytical batch, and the assays were done without knowledge of whether they were from affected or unaffected pregnancies.

Maternal serum hCG was assayed using an immunoradiometric assay (Serono-MAIA-clone kit calibrated to the first international reference preparation) at a 1 in 500 dilution. All the assays were performed within three days and cases and controls were always assayed in the same analytical batch without knowledge of whether the samples were from affected or unaffected pregnancies.

Results

Maternal Serum Unconjugated Oestriol

Figure 2:
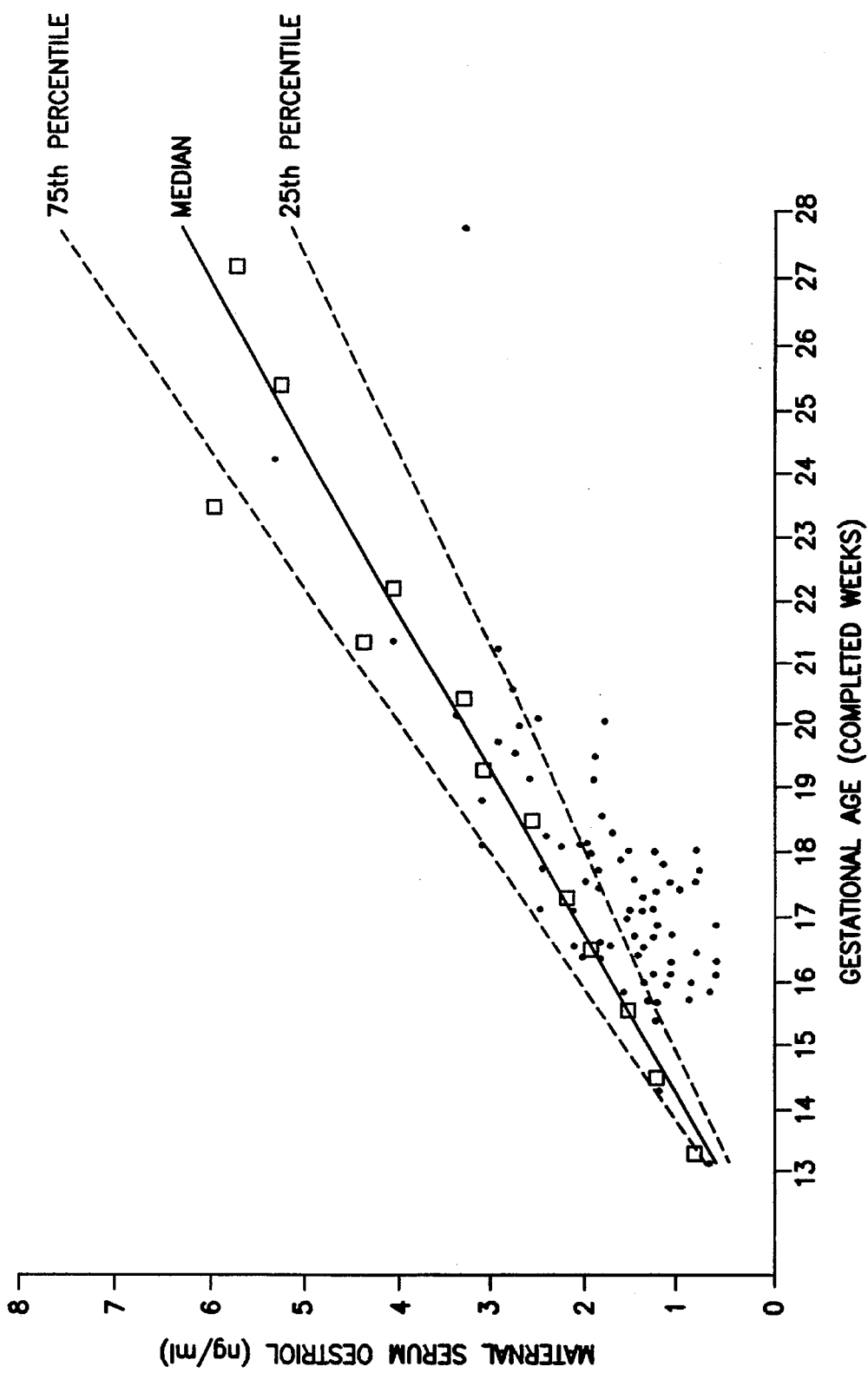
FIG. 2 is a graph showing individual patient maternal unconjugated serum oestriol levels for each pregnancy associated with Down's syndrome plotted against the gestational age of the fetus in weeks. Also shown are the median and 25th and 75th percentile values of serum oestriol levels for unaffected pregnancies during each week of gestation.

FIG. 2 shows the individual unconjugated oestriol levels for each pregnancy associated with Down's syndrome, together with the median and the 25th and 75th percentlie values for unaffected pregnancies, based on linear regressions on gestation weighted for the number of women tested in each week of gestation. The observed medians for unaffected pregnancies at each week of gestation are also shown. On average, the unconjugated oestriol values were significantly lower for the Down's syndrome pregnancies than for the unaffected pregnancies ($p<0.001$, by analysis of variance of the ranks within matched sets). There was no tendency for the difference to be materially different in any particular week from 13 to 27 weeks of gestation.

Unconjugated oestriol levels can conveniently be expressed in multiples of the median for unaffected pregnancies of the same gestational age (MoM) using the regressed medians shown in Table I below.

TABLE I

| Percentile | MSO (MoM) | |
|---|---|---|
| | Down's syndrome pregnancies (n = 77) | Unaffected pregnancies (n = 385) |
| 25th | 0.59 | 0.83 |
| 50th (median) | 0.73 | 1.00 |
| 75th | 0.90 | 1.19 |

MSO = maternal serum unconjugated oestriol

Table I shows the 25th, 50th and 75th percentlies of maternal serum unconjugated oestriol in MoMs for the Down's syndrome and unaffected pregnancies. The median serum AFP for the affected pregnancies was only 73% of the value for unaffected pregnancies ($p<0.001$).

Table II shows the proportion of Down's syndrome and unaffected pregnancies with median serum unconjugated oestriol levels less than or equal to specified cut-off levels. Gaussian frequency distributions fitted the data reasonably well.

TABLE II

| Unconjugated Oestriol Level (MoM) | Down's syndrome pregnancies (%) | Unaffected pregnancies (%) |
|---|---|---|
| ≦0.40 | 9.1 | 1.3 |
| ≦0.50 | 16 | 3.1 |
| ≦0.60 | 26 | 4.9 |
| ≦0.70 | 46 | 9.6 |
| ≦0.80 | 62 | 21 |
| ≦0.90 | 75 | 35 |
| ≦1.00 | 86 | 50 |

Table III shows the median maternal serum unconjugated oestriol (MSO) level in Down's syndrome and unaffected pregnancies according to maternal age. In both Down's syndrome and unaffected pregnancies the median serum unconjugated oestriol provides a measure of the risk of Down's syndrome that is independent of maternal age.

TABLE III

| Maternal age at expected date of delivery. (years) | Down's syndrome pregnancies | | Unaffected pregnancies | |
|---|---|---|---|---|
| | MSO (MoM) | Number | MSO (MoM) | Number |
| <30 | 0.75 | 20 | 0.98 | 100 |
| 30–34 | 0.72 | 17 | 1.04 | 85 |
| 35–39 | 0.76 | 19 | 1.00 | 95 |
| 40 or more | 0.73 | 21 | 1.00 | 105 |
| All | 0.73 | 77 | 1.00 | 385 |

Table IV shows that in both Down's syndrome and unaffected pregnancies the median maternal serum unconjugated oestriol level (MSO) increases with increasing maternal serum AFP level expressed like unconjugated oestriol in MoMs). The correlation between unconjugated oestriol and the log of AFP levels is statistically significant ($r=0.21$, $p<0.05$ for Down's syndrome pregnancies and $r=0.20$, $p<0.001$ for unaffected pregnancies). A bivariate Gaussian frequency distribution fitted the data reasonably well.

TABLE IV

| | Serum AFP level | | | |
|---|---|---|---|---|
| | Down's syndrome pregnancies | | Unaffected pregnancies | |
| (MoM) | MSO (MoM) | Number | MSO (MoM) | Number |
| ≦0.60 | 0.66 | 17 | 0.74 | 22 |
| 0.61–0.80 | 0.72 | 24 | 0.95 | 76 |
| 0.81–1.00 | 0.82 | 23 | 0.96 | 94 |
| >1.00 | 0.82 | 13 | 1.04 | 193 |
| All | 0.73 | 77 | 1.00 | 385 |

A way of combining information on median serum AFP and median serum unconjugated oestriol levels which gives equal weight to both tests is to regard a screening result as positive if either level is less than or equal to the same percentile of normal. Using this approach, for a given number of affected pregnancies with positive results there were fewer unaffected pregnancies with positive results when both tests were used than when each test was considered alone (Table V).

TABLE V

| Downs Syndrome Detectn. (%) | False-positive rate (%) using | | | | | |
|---|---|---|---|---|---|---|
| | Age alone (a) | AFP alone (b) | $uE_3$ alone (c) | Age & AFP (d) | Age & $uE_3$ (e) | Age, AFP and $uE_3$ (f) |
| 60 | 31 | 33 | 28 | 20 | 14 | 12 |
| 55 | 25 | 28 | 19 | 16 | 11 | 9.1 |
| 50 | 19 | 24 | 16 | 12 | 8.8 | 7.0 |
| 45 | 15 | 20 | 13 | 9.8 | 6.7 | 5.3 |
| 40 | 11 | 17 | 11 | 7.3 | 5.0 | 3.9 |
| 35 | 7.5 | 14 | 8.5 | 5.3 | 3.7 | 2.8 |
| 30 | 5.1 | 11 | 6.6 | 3.6 | 2.5 | 1.9 |
| 25 | 3.3 | 8.2 | 5.0 | 2.2 | 1.6 | 1.2 |
| 20 | 1.9 | 6.0 | 3.5 | 1.3 | 0.9 | 0.7 |

Note:
A result is positive if (a) age is advanced, (b) AFP is low, (c) $uE_3$ is low or, for (d), (e) and (f), the risk of Downs Syndrome (at term) is high.

Most of the saving achieved by doing both tests (AFP and MSO) compared to only one was due to the screening efficiency of unconjugated oestriol rather than AFP. For example, to identify 35% of Down's syndrome pregnancies as positive (see Table V), the use of both tests reduced the proportion of unaffected pregnancies with positive results by only 0.1% compared to that achieved with unconjugated oestriol alone but reduced the proportion by 2.2% compared to that achieved with AFP alone. Logistic regression analysis confirmed that unconjugated oestriol was a stronger predictor for Down's syndrome than AFP, though each provided additional information that was statistically significant ($X_1^2=45.4$, $p<0.0001$ for unconjugated oestriol added to AFP; $X_1^2=11.2$, $p<0.001$ for AFP added to unconjugated oestriol).

These results confirm that maternal serum unconjugated oestriol is, on average, lower in pregnancies associated with Down's syndrome than unaffected pregnancies, an effect Which is independent of maternal age. The results also show that a serum unconjugated oestriol level distinguished affected from unaffected pregnancies more effectively than a serum AFP level.

The explanation for the low maternal serum unconjugated oestriol levels in Down's syndrome pregnancies is unknown. FIG. 1 shows the metabolic pathway of oestriol biosynthesis in the foetus and placenta and indicates the sites at which a metabolic alteration could arise. In normal pregnancy, the foetal adrenal cortex produces DHEAS which enters the foetal circulation and passes to the foetal liver, where most of it undergoes 16-alpha-hydroxylation. The newly formed 16-hydroxy-DHEAS reaches the placenta where it is converted in four enzymatic steps (sulphatase, aromatase and 17-beta-hydroxysteroid dehydrogenase) to oestriol. Oestriol then diffuses into the maternal compartment, where it can be measured as an unconjugated steroid, its rise in concentration paralleling the growth of the foetus and the placenta. Unlike total oestriol, unconjugated oestriol in maternal serum is entirely derived from the foetus and the placenta. For this reason it use herein is a more sensitive indication of altered formal metabolism than the total maternal serum oestriol.

The introduction into the screening programme of a progesterone assay, giving four parameters as indicators of risk (maternal age, unconjugated oestriol, AFP and progesterone) further increases the degree of selectivity obtained.

It has also been found to be advantageous to include in the screening programme an assay for human chorionic gonadotrophin (hCG). The median maternal hCG level in seventy-seven pregnancies associated with Down Syndrome was twice the median level in 385 unaffected pregnancies matched for maternal age, gestational age and duration of serum sample storage ($p<0.001$). Maternal serum hCG measurement was therefore an effective screening test for Down's Syndrome. For example, to achieve a 30% detection rate, the false-positive (the proportion of unaffected pregnancies classified as positive) was 3% for hCG, lower than for maternal age (5%) and unconjugated oestriol (7%) and AFP (11%). The most effective screen was achieved by taking account of all four of these parameters; to achieve the same 30% detection rate, the false-positive rate declined to 0.5%.

Combining Screening Tests

When using several variables in combination to screen for a particular disorder it is necessary to assess the extent of the correlation between the variables concerned. If two variables are perfectly correlated one adds nothing to the other in assessing a subject's risk of having the disorder; if they are completely Unrelated each provides an independent measure of risk. To the extent that they may be partially correlated there will be some independent information. The associations between hCG, uE$_3$ and AFP in affected and unaffected pregnancies are shown in Table VI below.

TABLE VI

|  | Down's Syndrome Pregnancies Median (No) hCG (MoM) | Unaffected Pregnancies Median (No) hCG (MoM) |
|---|---|---|
| Age (years) | | |
| <30 | 1.94 (20) | 1.10 (100) |
| 30– | 1.62 (17) | 0.96 (85) |
| 35– | 2.11 (19) | 0.95 (95) |
| ≧40 | 2.19 (21) | 1.02 (105) |
| uE$_3$ (MoM) | | |
| <0.60 | 2.71 (20) | 1.25 (19) |
| 0.60– | 1.88 (20) | 1.21 (36) |
| 0.75– | 1.85 (18) | 0.97 (77) |
| ≧0.90 | 1.84 (19) | 1.00 (253) |
| AFP (MoM) | | |
| <0.60 | 1.64 (17) | 1.02 (22) |
| 0.60– | 2.05 (24) | 0.91 (75) |
| 0.80– | 2.12 (23) | 0.89 (95) |
| ≧1.00 | 2.24 (13) | 1.10 (193) |
| All | 2.04 (77) | 1.02 (385) |

These results indicate no evidence of an association between hCG levels and maternal age, but there is a small negative association between hCG and unconjugated oestriol (uE$_3$) levels. The relationship between hCG and AFP is less evident, but since uE$_3$ and AFP have previously been shown to be associated, and hCG and uE$_3$ are, there is probably an underlying association.

Table VII shows the risk of having a Down's Syndrome pregnancy according to selected values of the three biochemical screening tests (maternal serum AFP, unconjugated oestriol and hCG) as they apply to a 35 year old woman.

TABLE VII

| uE$_3$ (MoM) | hCG (MoM) | AFP (MoM) | | |
|---|---|---|---|---|
| | | 0.4 | 1.0 | 2.5 |
| 0.4 | 0.5 | 1:370 | 1:2800 | 1:22000 |
| | 1.0 | 1:84 | 1:480 | 1:2800 |
| | 2.0 | 1:16 | 1:69 | 1:310 |
| 1.0 | 0.5 | 1:820 | 1:4800 | 1:28000 |
| | 1.0 | 1:330 | 1:1400 | 1:6400 |
| | 2.0 | 1:110 | 1:360 | 1:1200 |
| 1.4 | 0.5 | 1:2200 | 1:11000 | 1:52000 |
| | 1.0 | 1:1300 | 1:4600 | 1:17000 |
| | 2.0 | 1:630 | 1:1700 | 1:4700 |

The results in Table VII show that if the results of any two tests are known, the third is still informative. For example, if a 35 year old woman had an AFP level of 1.0 MoM and an uE$_3$ level of 0.4 MoM, the risk would be 1:2800 at a hCG level of 0.5 MoM and 1:69 at 2.0 MoM hCG.

If only two tests are to be carried out, AFP and hCG are the preferred pair since AFP is of separate value in screening for neural tube defects and the performance of AFP and hCG in combination is not much worse than that using uE$_3$ and hCG in combination. The best overall results however are obtained using all three tests, together with maternal age. This, for example, yielded a detection rate of 60% with a false-positive rate of 47% (see below).

Table VIII summarises the rate of false positive detection corresponding to Down's Syndrome detection rates using maternal age in conjuction with assays for unconjugatedoestriol (uE$_3$), AFP, and hGC alone or in combination.

TABLE VIII

| Down Syndrome Detection Rate (%) | False-positive rate (%) using age with: | | | | | | |
|---|---|---|---|---|---|---|---|
| | AFP | uE$_3$ | hCG | AFP and uE$_3$ | AFP and hCG | uE$_3$ and hCG | AFP, uE$_3$ and hCG |
| 80 | 44 | 34 | 27 | 29 | 20 | 20 | 16 |
| 75 | 37 | 27 | 21 | 23 | 15 | 15 | 12 |
| 70 | 30 | 22 | 16 | 18 | 12 | 11 | 8.6 |
| 65 | 25 | 18 | 12 | 15 | 8.8 | 8.1 | 6.4 |
| 60 | 20 | 14 | 9.5 | 12 | 6.7 | 6.0 | 4.7 |
| 55 | 16 | 11 | 7.2 | 9.1 | 5.0 | 4.4 | 3.4 |
| 50 | 12 | 8.8 | 5.4 | 7.0 | 3.7 | 3.2 | 2.5 |
| 45 | 9.7 | 6.7 | 3.9 | 5.3 | 2.7 | 2.3 | 1.7 |
| 40 | 7.3 | 5.0 | 2.8 | 3.9 | 1.9 | 1.6 | 1.2 |
| 35 | 5.3 | 3.7 | 1.9 | 2.8 | 1.3 | 1.0 | 0.8 |
| 30 | 3.6 | 2.5 | 1.2 | 1.9 | 0.8 | 0.7 | 0.5 |
| 25 | 2.2 | 1.6 | 0.8 | 1.2 | 0.5 | 0.4 | 0.3 |
| 20 | 1.3 | 0.9 | 0.4 | 0.7 | 0.3 | 0.2 | 0.2 |

Table IX below summarises the rate of detection at false-positive rate using a variety of assays alone or in combination. The abbreviations used in the first column are as follows:

A=(log$_{10}$) alpha-fetoprotein (AFP); E=unconjugated oestriol; H=(log$_{10}$) human chorionic gonadotrophin (hCG); P=(log$_{10}$) progesterone

TABLE IX

| Meas | Without DHEAS | | | | With DHEAS | | | |
|---|---|---|---|---|---|---|---|---|
| | d | Risk | % Det | PPV | d | Risk | % Det | PPV |
| AEHP | 1.771 | 232 | 63.6 | 62 | 1.795 | 232 | 64.3 | 61 |
| AEH | 1.680 | 227 | 60.6 | 65 | 1.700 | 228 | 61.3 | 64 |
| EHP | 1.601 | 226 | 58.1 | 68 | 1.632 | 226 | 59.1 | 67 |
| AEP | 1.585 | 225 | 57.5 | 68 | 1.619 | 226 | 58.7 | 67 |
| EH | 1.539 | 225 | 56.1 | 70 | 1.565 | 225 | 56.9 | 69 |
| AHP | 1.517 | 225 | 55.4 | 71 | 1.546 | 225 | 56.3 | 70 |
| AH | 1.493 | 225 | 54.6 | 72 | 1.519 | 225 | 55.5 | 71 |
| EP | 1.390 | 227 | 51.4 | 76 | 1.434 | 226 | 52.8 | 75 |
| HP | 1.272 | 231 | 47.9 | 82 | 1.312 | 229 | 49.1 | 80 |
| H | 1.268 | 231 | 47.8 | 82 | 1.305 | 229 | 48.8 | 80 |
| AE | 1.159 | 237 | 44.7 | 88 | 1.193 | 235 | 45.6 | 86 |
| AP | 1.080 | 243 | 42.6 | 92 | 1.133 | 239 | 44.0 | 89 |
| E | 1.006 | 249 | 40.7 | 96 | 1.051 | 246 | 41.9 | 94 |
| A | 0.703 | 285 | 34.7 | 113 | 0.767 | 277 | 35.8 | 110 |
| P | 0.656 | 291 | 34.0 | 116 | 0.753 | 278 | 35.5 | 111 |
| DHEAS | — | — | — | — | 0.333 | 321 | 30.7 | 128 | d = distance, in standard deviation units, between affected and unaffected groups.
Risk is quoted as a ratio of 1: the figure in the Table.
PPV = positive predictive value and is an indicator of the odds of the actual occurrence of Down's Syndrome in the foetus. It is quoted as a ratio of 1: the figure in the Table.

In many existing screening programmes about 5% of women are selected for amniocentesis on the basis of advanced age alone. The method of this invention using assays for AFP, hCG, and unconjugated oestriol, in combination with maternal age detects over 60% of affected pregnancies, more than double that achievable with the same amniocentesis rate in existing screening programmes. As an illustration, this method has the potential to reduce the number of Down Syndrome births in the United Kingdom from about 900 per year, in the absence of screening, to about 350 per year.

The rate of detection may be further enhanced by ultrasound screening, using, for example, fetal femur length measurement as a complementary technique.

We claim:

1. An assay kit for a sample of serum from a pregnant woman at a stage before the beginning of the third trimester of pregnancy to determine if a pregnant woman is carrying a fetus having an increased risk of Down's syndrome, said kit consisting of:

an immunoassay means to determine a level of unconjugated oestriol in said sample, an immunoassay means to determine a level of alpha-fetoprotein in said sample, and an immunoassay means to determine a level of human chorionic gonadotrophin in said sample.

2. An assay kit for a sample of serum from a pregnant woman at a stage before the beginning of the third trimester of pregnancy to determine if a pregnant woman is carrying a fetus having an increased risk of Down's syndrome, said kit consisting of:

an immunoassay means to determine a level of unconjugated oestriol in said sample, an immunoassay means to determine a level of dehydroepiandrosterone sulfate in said sample, an immunoassay means to determine a level of alpha-fetoprotein in said sample, and an immunoassay means to determine a level of human chorionic gonadotrophin in said sample.

3. An assay kit for a sample of serum from a pregnant woman at a stage before the beginning of the third trimester of pregnancy to determine if a pregnant woman is carrying a fetus having an increased risk of Down's syndrome, said kit consisting of:

an immunoassay means to determine a level of dehydroepiandrosterone sulfate in said sample, an immunoassay means to determine a level of alpha-fetoprotein in said sample, and optionally an immunoassay means to determine a level of human chorionic gonadotrophin in said sample.

* * * * *